(12) United States Patent
Li et al.

(10) Patent No.: US 10,499,833 B2
(45) Date of Patent: Dec. 10, 2019

(54) WEARABLE DEVICE AND METHOD FOR MONITORING EATING

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Mubing Li, Beijing (CN); Chungchun Chen, Beijing (CN); Haisheng Wang, Beijing (CN); Xiaochuan Chen, Beijing (CN); Xue Dong, Beijing (CN); Jiantao Liu, Beijing (CN); Jinghua Miao, Beijing (CN); Changfeng Li, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 671 days.

(21) Appl. No.: 15/023,547

(22) PCT Filed: Sep. 23, 2015

(86) PCT No.: PCT/CN2015/090325
§ 371 (c)(1),
(2) Date: Mar. 21, 2016

(87) PCT Pub. No.: WO2016/192251
PCT Pub. Date: Dec. 8, 2016

(65) Prior Publication Data
US 2017/0156634 A1    Jun. 8, 2017

(30) Foreign Application Priority Data

Jun. 3, 2015  (CN) .......................... 2015 1 0300296

(51) Int. Cl.
*A61B 5/11* (2006.01)
*G09B 19/00* (2006.01)
(Continued)

(52) U.S. Cl.
CPC .............. *A61B 5/11* (2013.01); *A61B 5/1123* (2013.01); *G09B 19/0092* (2013.01);
(Continued)

(58) Field of Classification Search
CPC ..... G06F 19/3475; G06F 1/163; A61B 5/681; A61B 5/6824; A61B 2562/0219;
(Continued)

(56) References Cited

U.S. PATENT DOCUMENTS

2002/0109600 A1  8/2002  Mault et al.
2004/0082840 A1*  4/2004  Chen .................... A61B 5/0002
600/300

(Continued)

FOREIGN PATENT DOCUMENTS

CN    101326526 A    12/2008
CN    102835951 A    12/2012
(Continued)

OTHER PUBLICATIONS

First Office Action regarding Chinese application No. 201510300296. 3, dated Oct. 9, 2016. Translation provided by Dragon Intellectual Property Law Firm.
(Continued)

*Primary Examiner* — Jerry-Daryl Fletcher
(74) *Attorney, Agent, or Firm* — Harness, Dickey & Pierce, P.L.C.

(57) ABSTRACT

A wearable device and a method for monitoring eating are provided. The wearable device is wearable on an arm of a user and includes: an acceleration sensor, used to acquire acceleration information of the arm of the user; a processing
(Continued)

unit connected to the acceleration sensor, used to calculate times of eating performed by the user in a predetermined duration based on the acceleration information and obtain an eating frequency of the user; a comparing unit connected to the processing unit, used to compare the eating frequency with a reference frequency and generate a first alarming signal if determining through comparison that the eating frequency is equal to or larger than the reference frequency; and an alarm connected to the comparing unit, used to alarm upon reception of the first alarming signal.

10 Claims, 5 Drawing Sheets

(51) Int. Cl.
  *G16H 20/60* (2018.01)
  *A61B 5/00* (2006.01)
(52) U.S. Cl.
  CPC ............ *G16H 20/60* (2018.01); *A61B 5/6824* (2013.01); *A61B 5/746* (2013.01)
(58) Field of Classification Search
  CPC ... A61B 5/4205; A61B 5/4542; A61B 5/1114; G09B 19/0092; G09B 19/00
  USPC ......................................................... 434/127
  See application file for complete search history.

(56) References Cited

U.S. PATENT DOCUMENTS

| | | | | |
|---|---|---|---|---|
| 2010/0194573 A1* | 8/2010 | Hoover | ................. | A61B 5/1123 340/573.1 |
| 2011/0199205 A1 | 8/2011 | Kreml | | |
| 2014/0347491 A1* | 11/2014 | Connor | ................. | A61B 5/1114 348/158 |
| 2014/0349256 A1* | 11/2014 | Connor | .............. | G09B 19/0092 434/127 |
| 2014/0349257 A1* | 11/2014 | Connor | .............. | G09B 19/0092 434/127 |

FOREIGN PATENT DOCUMENTS

| | | |
|---|---|---|
| CN | 102920461 A | 2/2013 |
| CN | 104068720 A | 10/2014 |
| CN | 104146446 A | 11/2014 |
| JP | 2000245713 A | 9/2000 |
| JP | 2011115508 A | 6/2011 |
| JP | 2014180335 A | 9/2014 |

OTHER PUBLICATIONS

Written Opinion of the International Searching Authority for international application No. PCT/CN2015/090325.

* cited by examiner (1)                                                   (2)

WEARABLE DEVICE AND METHOD FOR MONITORING EATING

CROSS-REFERENCE TO RELATED APPLICATION

The present application is the U.S. national phase of PCT Application No. PCT/CN2015/090325 filed on Sep. 23, 2015, which claims a priority to Chinese Patent Application No. 201510300296.3 filed on Jun. 3, 2015, the disclosure of which is incorporated in its entirety by reference herein.

TECHNICAL FIELD

The present disclosure relates to the technical field of wearable devices, in particular, to a wearable device and a method for monitoring eating.

BACKGROUND

Gastrointestinal diseases are common, which have high morbidities in cities of large and medium sizes and fast living tempo. There are various factors resulting in gastrointestinal diseases, among which eating too fast is a common one. Therefore, it is an urgent technical problem to be solved how to monitor an eating speed of an eater effectively.

SUMMARY

In view of the above, a wearable device and a method for monitoring eating are provided in the present disclosure, which can effectively monitor an eating frequency of a user and prompt the user when the user eats too fast.

To solve the above technical problems, a wearable device is provided in the present disclosure, including: an acceleration sensor, used to acquire acceleration information of the arm of the user; a processing unit connected to the acceleration sensor, used to calculate times of eating performed by the user in a predetermined duration based on the acceleration information and obtain an eating frequency of the user; a comparing unit connected to the processing unit, used to compare the eating frequency with a reference frequency and generate a first alarming signal if determining through comparison that the eating frequency is equal to or larger than the reference frequency; and an alarm connected to the comparing unit, used to alarm upon reception of the first alarming signal.

Optionally, the wearable device further includes a display unit, connected to the comparing unit and used to display the eating frequency of the user upon reception of the first alarming signal.

Optionally, the wearable device further includes a calculating unit connected to the processing unit, used to calculate an average eating frequency of the user within a preset test period and set the average eating frequency as the reference frequency; and a storage connected to the calculating unit, used to store the reference frequency.

Optionally, the wearable device further includes a mode setting unit, used to set a test mode and an eating monitoring mode, and a controller connected to the mode setting unit, used to control the calculating unit to operate and control the comparing unit not to operate when the test mode is set, and control the comparing unit to operate and control the calculating unit not to operate when the eating monitoring mode is set.

Optionally, the wearable device further includes a frequency setting unit used to provide a frequency setting interface for the user to set the reference frequency, and a storage connected to the frequency setting unit and configured to store the reference frequency.

Optionally, the wearable device further includes a controlling switch, used to generate an on signal under control of the user and generate an off signal under control of the user, and a battery unit connected to the controlling switch, the acceleration sensor, the processing unit and the alarm, used to provide electricity to the acceleration sensor, the processing unit and the alarm upon reception of the on signal and stop providing electricity to the acceleration sensor, the processing unit and the alarm upon reception of the off signal.

Optionally, the wearable device further includes a counter connected to the processing unit, used to count total times of eating of the user after being provided with electricity and generate a second alarming signal if the total times of eating exceed a preset threshold. The alarm is further configured to alarm upon reception of the second alarming signal. The alarm alarms, upon reception of the second alarming signal, in a different way from alarming upon reception of the first alarming signal.

Optionally, the alarm is a vibration alarm, an audio alarm, a caution light or a display unit.

Optionally, the wearable device is a bracelet.

A method for monitoring eating is further provided in the present disclosure. The method is applied to the foregoing wearable device and includes: acquiring acceleration information of the arm of the user; calculating times of eating performed by the user within a preset duration based on the acceleration information and obtaining the eating frequency of the user; comparing the eating frequency with a reference frequency, and generating a first alarming signal if determining through comparison that the eating frequency is larger than or equal to the reference frequency; and alarming upon reception of the first alarming signal.

A wearable device is further provided in the present disclosure, which is wearable on an arm of a user and includes an acceleration sensor, an amplifier-filter, an analog-to-digital converter, a microprogrammed control unit (MCU), a random access memory, a digital-to-analog converter, an alarm and a display unit.

The acceleration sensor is used to acquire acceleration information of the arm of the user and convert the acceleration information into an analog electric signal.

The amplifier-filter is connected to the acceleration sensor and used to amplify and filter the received analog electric signal.

The analog-to-digital converter is connected to the amplifier-filter and used to convert an analog electric signal already amplified and filtered by the amplifier-filter into a digital signal.

The MCU is used to calculate times of eating of the user within a predetermined duration based on the digital signal, compare the eating frequency with a reference frequency, and generate a first alarming signal if it is determined through comparison that the eating frequency is larger than or equal to the reference frequency.

The random access memory is connected to the MCU and used to store the reference frequency.

The digital-to-analog converter is connected to the MCU and used to convert the eating frequency of the user into an analog signal and send the analog signal to the display unit.

The display unit is connected to the digital-to-analog converter and used to display the eating frequency.

The alarm is connected to the MCU and used to alarm in response to the first alarming signal.

The above technical solution of the present disclosure has the following beneficial effects.

Times of eating performed by the user in the predetermined duration are calculated by acquiring and analyzing the acceleration information of the arm of the user, thereby obtaining the eating frequency of the user. It is determined whether the user eats too fast based on the eating frequency of the user, and alarming is performed if the user eats too fast to timely prompt the user to adjust the eating speed, thereby avoiding gastrointestinal diseases.

DETAILED DESCRIPTION OF THE EMBODIMENTS

Figure 1:
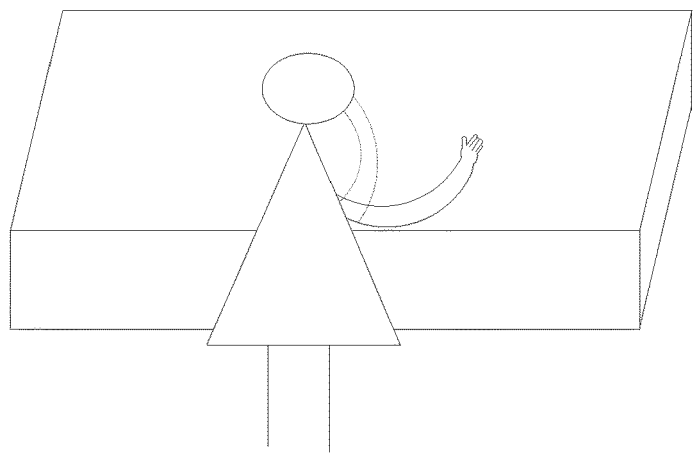
FIG. 1 schematically shows a waving state of an arm of an eater while eating.

Reference can be made to FIG. 1, which schematically shows a waving state of an arm of an eater while eating. As shown in FIG. 1, a waving range of the arm is about one forth of a circle when the eater eats. The arm waves with a changing acceleration.

Figure 2:
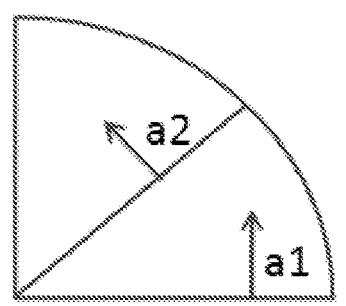
FIG. 2 schematically shows change of an acceleration of a waving arm of an eater while eating.
Figure 2:
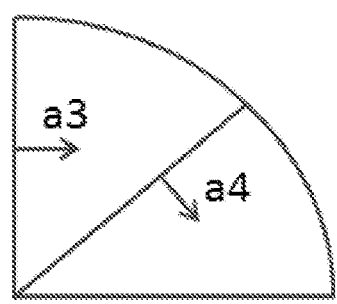

Reference can be made to FIG. 2, which schematically shows change of an acceleration of a waving arm of an eater while eating. FIG. 2 (1) shows change of an acceleration of an arm waving upwardly. As shown in FIG. 2 (1), an acceleration (a1) in a vertical direction is generated when the arm waves upwardly. As the arm waves upwardly, the acceleration in the vertical direction changes (a2) and turns into 0 when reaching a vertex. FIG. 2 (2) shows change of an acceleration of an arm waving downwardly. As shown in FIG. 2 (2), an acceleration (a3) in a horizontal direction is generated when the arm waves downwardly. As the arm waves downwardly, the acceleration in the horizontal direction changes (a4) and turns into 0 when reaching a horizontal position.

In the present disclosure, acceleration information of an arm of a user (i.e., the eater) can be acquired by an acceleration sensor. Different sine curves can be plotted according to different changes of acceleration. When a change from a crest to a trough takes place in the vertical direction and a change from a crest to a trough takes place in the horizontal direction, the eater accomplishes one time of eating. That is, times of eating performed by the eater can be calculated based on statistics for the change of the acceleration. Furthermore, an eating frequency of the eater can be obtained by calculating times of eating performed by the eater per unit time. It can be determined whether the eater eats too fast by comparing the eating frequency of the eater with a reference frequency. An alarming is performed when the eater eats too fast, thereby prompting the eater timely to adjust an eating speed and avoiding gastrointestinal diseases.

Specific implementations of the present disclosure are further detailed based on embodiments in conjunction with drawings. The following embodiments are used for explaining, rather than limiting the present disclosure.

Figure 3:
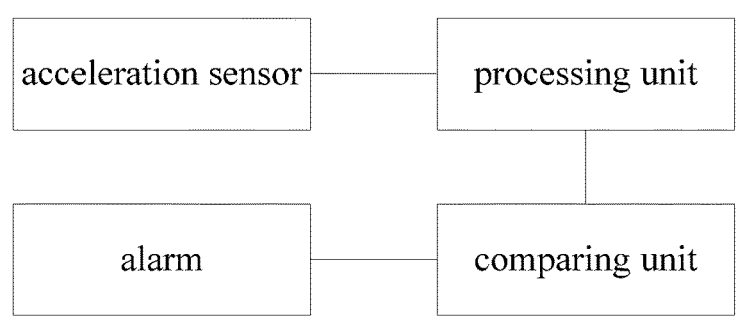
FIG. 3 is a schematic structural diagram of a wearable device according to a first embodiment of the present disclosure.

As shown in FIG. 3, a wearable device according to one embodiment of the present disclosure, which can be worn on the arm of the user, includes: an acceleration sensor, which is used to acquire acceleration information of the arm of the user; a processing unit connected to the acceleration sensor, and used to calculate times of eating performed by the user in a predetermined duration, i.e., an eating frequency, based on the acceleration information; a comparing unit connected to the processing unit, and used to compare the eating frequency with a reference frequency, and generate a first alarming signal if it is determined through the comparison that the eating frequency is equal to or larger than the reference frequency; and an alarm connected to the comparing unit, and used to alarm upon reception of the first alarming signal.

With the wearable device according to the embodiment of the present disclosure, times of eating performed by the user in the predetermined duration can be calculated by acquiring and analyzing the acceleration information of the arm of the user, thereby obtaining the eating frequency of the user. It is determined whether the user eats too fast based on the eating frequency of the user, alarming is performed if the user eats too fast to timely prompt the user to adjust the eating speed, thereby avoiding gastrointestinal diseases.

The acceleration sensor according to the embodiment of the present disclosure can acquire acceleration information in the horizontal direction and the vertical direction and transfer the acceleration information to the processing unit. The processing unit analyzes changes of accelerations in the horizontal direction and the vertical direction, and one time of eating is recorded as accomplished when the acceleration in the vertical direction has a change from a crest to a trough and the acceleration in the horizontal direction has a change from a crest to a trough. Times of eating performed by the user within a predetermined duration (e.g., 30 seconds) are calculated to obtain an eating frequency. The eating frequency can be represented by "8 times per 30 seconds" or by a directly calculated value of frequency "0.27 times per second".

The comparing unit according to the embodiment of the present disclosure compares a current eating frequency of the user with the reference frequency. The reference frequency can be represented by "5 times per 30 seconds". Actually, it is only needed to compare times of eating (for example, comparing 8 with 5). Alternatively, the reference frequency can also be represented by "0.17 times per second", and values of frequencies are compared (for example, comparing 0.27 with 0.17). If it is determined through comparison that the eating frequency is larger than or equal to the reference frequency, the first alarming signal is generated.

The alarm according to the embodiment of the present disclosure can be embodied as a vibration alarm, an audio alarm, a caution light, or the like.

Optionally, the wearable device according to the embodiment of the present disclosure may further include a display unit, which is connected to the comparing unit and used to display the eating frequency of the user upon reception of the first alarming signal. Optionally, displayed eating frequency information may include contents such as "the current eating frequency is 8 times per 30 seconds", such that the user can see the eating frequency information and take it as reference for adjusting the eating speed. In addition, the display unit may alarm as an alarm, for example, the display unit glitters and displays contents such as "the eating speed is too high", which is easily seen by the user.

The wearable device according to the embodiment of the present disclosure may be a bracelet or a watch, and may include two operating modes: a time displaying operating mode and an eating monitoring mode. In the time displaying operating mode, the wearable device displays time information and the acceleration sensor, the processing unit, the comparing unit and the alarm do not operate. In the eating monitoring mode, the acceleration sensor, the processing unit, the comparing unit and the alarm operate and the wearable device monitors eating.

Figure 9:
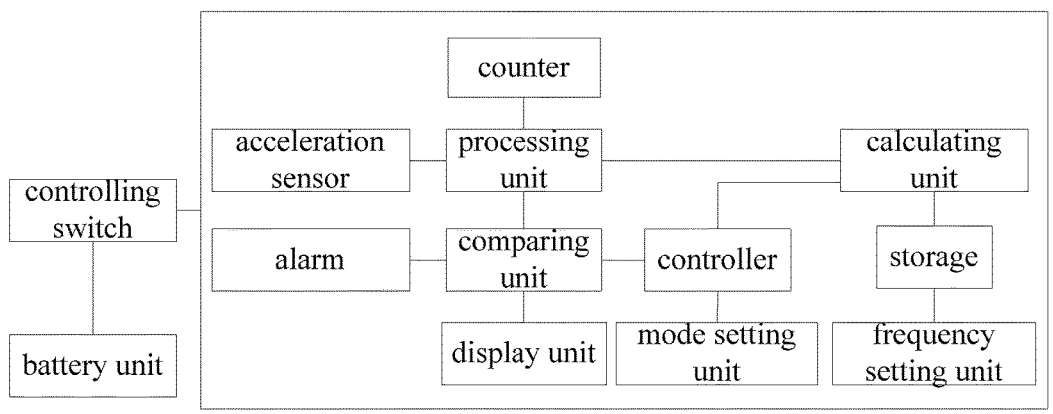
FIG. 9 is a schematic structural diagram of a wearable device according to one embodiment of the present disclosure.

The reference frequency can be obtained in various ways. For example, in a first way, the reference frequency is preset before leaving the factory and is stored in the wearable device. In a second way, a frequency setting unit is provided in the wearing device, and as shown in FIG. 9, the frequency setting unit may provide a frequency setting interface for the user to set the reference frequency. In a third way, the wearable device performs statistics on eating frequencies of the user within a preset test period (e.g., one week or one month) and takes an average eating frequency within the preset test period as the reference frequency.

When the third way is used, optionally as shown in FIG. 9, the wearable device further includes: a calculating unit connected to the processing unit, and used to calculate the average eating frequency of the user within the preset test period and set the average eating frequency as the reference frequency; and, a storage connected to the calculating unit, and used to store the reference frequency.

Further optionally, as shown in FIG. 9, the wearable device may include a mode setting unit used to set a test mode and an eating monitoring mode, and a controller connected to the mode setting unit. The controller is used to control the calculating unit to operate and control the comparing unit not to operate if the test mode is set, and to control the comparing unit to operate and control the calculating unit not to operate if the eating monitoring mode is set.

That is to say, in one preset test period, it is not determined whether the user eats fast or slowly and no alarming is performed, while only the eating frequency is recorded. In the eating monitoring mode, it is determined whether the user eats fast or slowly and the alarming is performed accordingly.

When the second way is used, as shown in FIG. 9, the wearable device optionally includes: a frequency setting unit used to provide a frequency setting interface for the user to set the reference frequency, and a storage connected to the frequency setting unit and used to store the reference frequency.

The wearable device according to the embodiment of the present disclosure only operates and performs an eating monitoring when the user dines. Consequently, as shown in FIG. 9, the wearable device optionally includes: a controlling switch, which is used to generate an on signal under control of the user and generate an off signal under control of the user; and a battery unit, which is used to provide electricity to functional components for eating monitoring in the wearable device upon reception of the on signal and stop providing electricity to the functional components for eating monitoring in the wearable device upon reception of the off signal. In this way, electric power of the wearable device can be effectively saved and false alarms can be avoided.

The wearable device according to the embodiments can monitor whether the user eats fast or not. It is understood that a total food-intake each meal also affects gastrointestinal health of the user. Hence, as shown in FIG. 9, the wearable device according to the embodiment of the present disclosure optionally includes a counter connected to the processing unit. The counter is used to count total times of eating of the user after being provided with electricity and generate a second alarming signal if the total time exceeds a preset threshold.

The alarm is further used to alarm upon reception of the second alarming signal. The alarm alarms, upon reception of the second alarming signal, in a different way from alarming upon reception of the first alarming signal. For example, the alarm sounds "dudu" when the user eats too fast and sounds "didi" when the user eats too much.

Figure 4:
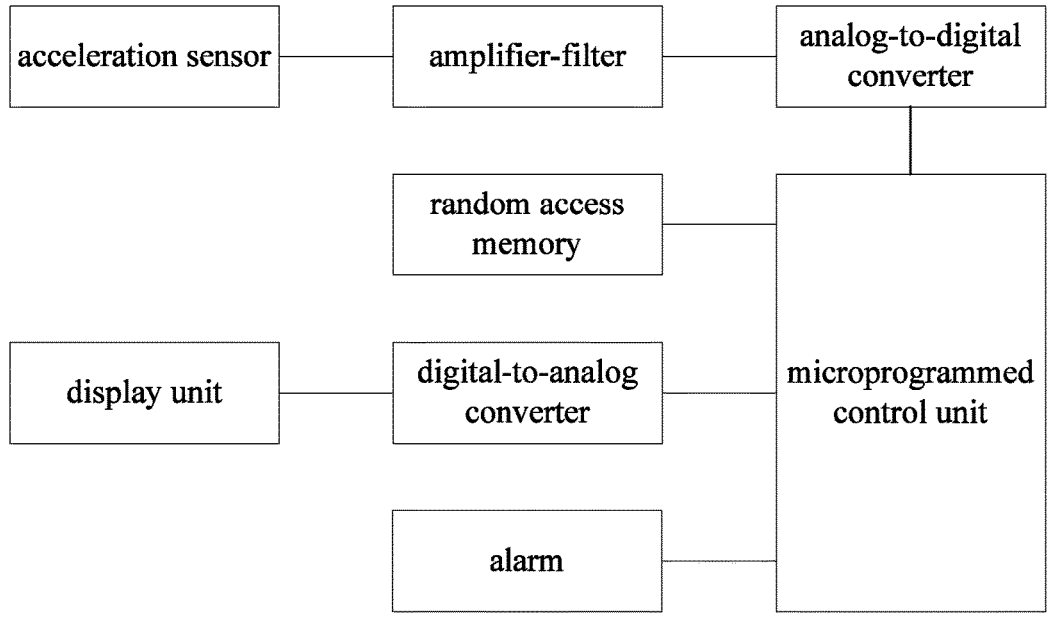
FIG. 4 is a schematic structural diagram of a wearable device according to a second embodiment of the present disclosure.

Reference can be made to FIG. 4, which is a schematic structural diagram of a wearable device according to a second embodiment of the present disclosure. The wearable device according to the embodiment of the present disclosure includes: an acceleration sensor, an amplifier-filter, an analog-to-digital converter, a microprogrammed control unit (MCU), a random access memory, a digital-to-analog converter, an alarm and a display unit.

The acceleration sensor according to the embodiment has a same function as the acceleration sensor according to the foregoing embodiment, which is used to acquire acceleration information of an arm of a user and convert the acceleration information into an analog electric signal.

The amplifier-filter is connected to the acceleration sensor and is used to amplify and filter the received analog electric signal.

The analog-to-digital converter is connected to the amplifier-filter and is used to convert an analog electric signal already amplified and filtered by the amplifier-filter into a digital signal.

The MCU performs functions of the processing unit and the comparing unit according to the foregoing embodiment. The MCU is used to calculate times of eating of the user within a predetermined duration based on the digital signal (the acceleration information), compare the eating frequency with a reference frequency, and generate a first alarming signal if it is determined through comparison that the eating frequency is larger than or equal to the reference frequency.

The random access memory is connected to the MCU and is used to store the reference frequency.

The digital-to-analog converter is connected to the MCU and is used to convert the eating frequency of the user into an analog signal and send the analog signal to the display unit.

The display unit is connected to the digital-to-analog converter and is used to display the eating frequency.

The alarm performs a function similar to the alarm according to the foregoing embodiment. The alarm is connected to the MCU and is used to alarm in response to the first alarming signal.

Figure 5:
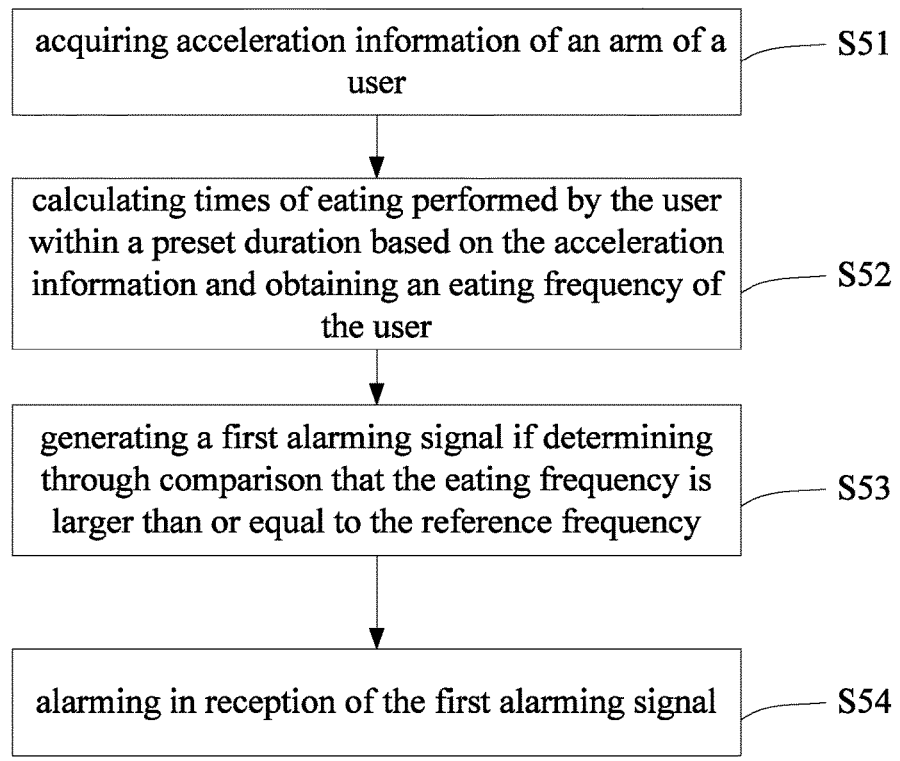
FIG. 5 is a schematic flow chart of a method for monitoring eating according to one embodiment of the present disclosure.

A method for monitoring eating, applied to the foregoing wearable device, is further provided in the present disclosure. As shown in FIG. 5, the method includes: step S51, acquiring acceleration information of an arm of a user; step S52, calculating times of eating performed by the user within a preset duration based on the acceleration information and obtaining an eating frequency of the user; step S53, comparing the eating frequency with a reference frequency, and generating a first alarming signal if it is determined through comparison that the eating frequency is larger than or equal to the reference frequency; and step S54, alarming upon reception of the first alarming signal.

Figure 6:
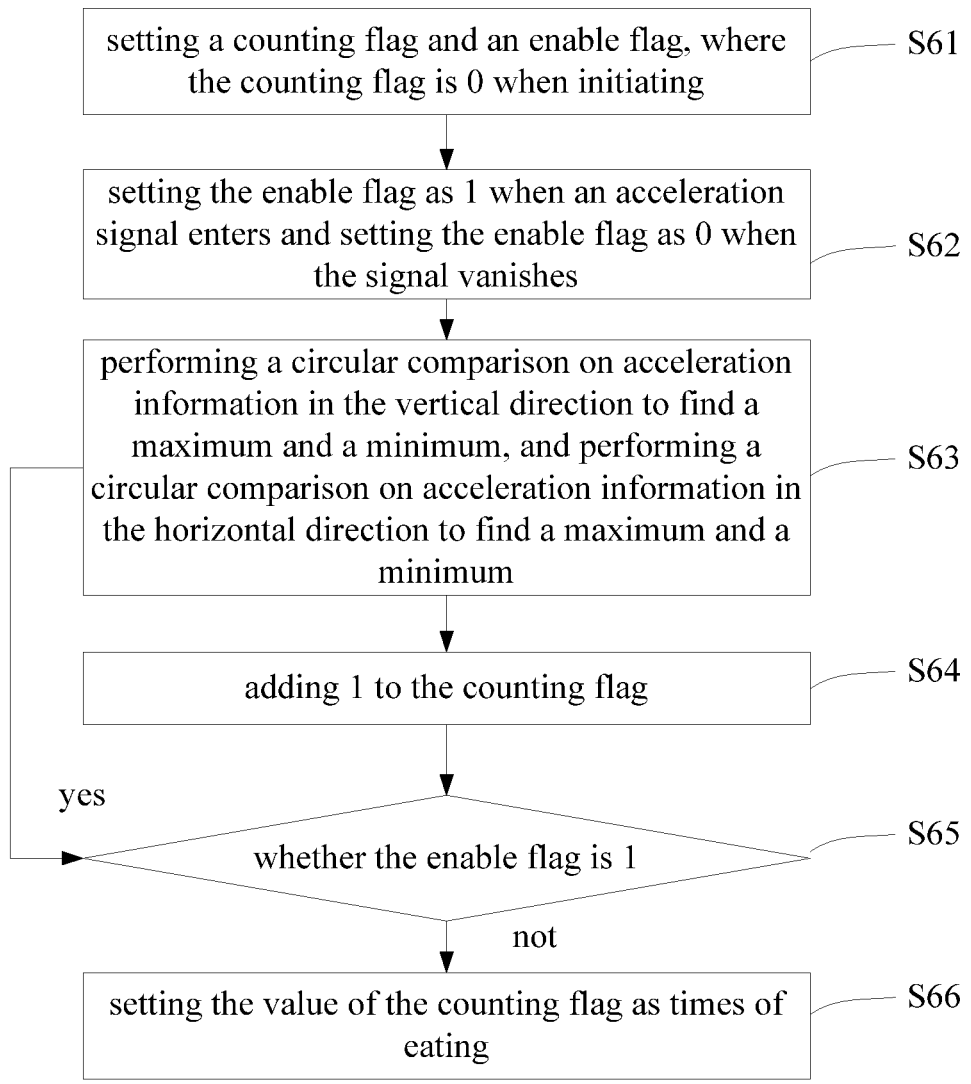
FIG. 6 is a schematic flow chart of an approach for converting acceleration information into times of eating according to one embodiment of the present disclosure.

Reference can be made to FIG. 6, which is schematic flow chart of an approach for converting the acceleration information into times of eating according to one embodiment of the present disclosure.

The approach includes: step S61, setting a counting flag and an enable flag, where the counting flag is 0 when initiating; step S62, setting the enable flag as 1 when an acceleration signal enters and setting the enable flag as 0 when the signal vanishes; step S63, performing a circular comparison on acceleration information in the vertical direction to find a maximum and a minimum, and performing a circular comparison on acceleration information in the horizontal direction to find a maximum and a minimum; step S64, adding 1 to the counting flag; step S65, determining whether the enable flag is 1, proceeding to step S63 if the enable flag is 1 until the enable flag is 0, or proceeding to step S66 if the enable flag is not 1; and step S66, setting the value of the counting flag as times of eating.

Figure 7:
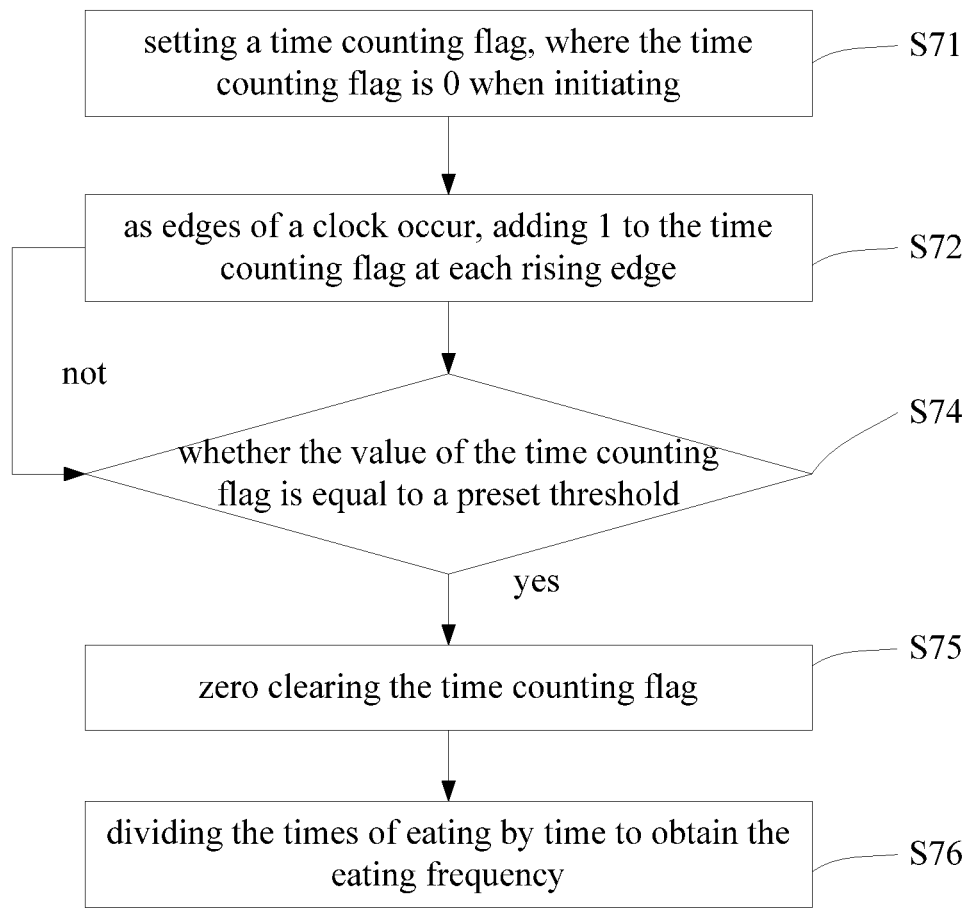
FIG. 7 is a schematic flow chart of an approach for calculating an eating frequency according to one embodiment of the present disclosure.

Reference can be made to FIG. 7, which is schematic flow chart of an approach for calculating the eating frequency according to one embodiment of the present disclosure.

The approach includes: step S71, setting a time counting flag, where the time counting flag is 0 when initiating; step S72, as edges of a clock occur, adding 1 to the time counting flag at each rising edge (for example, each rising edge represents 1 second); step S73, determining whether the value of the time counting flag is equal to a preset threshold, executing step S74 and S75 if the value of the time counting flag is equal to the preset threshold, or proceeding to step S72 if the value of the time counting flag is not equal to the preset threshold; step S74, zero clearing the time counting flag; and step S75, dividing the times of eating by time to obtain the eating frequency.

Figure 8:
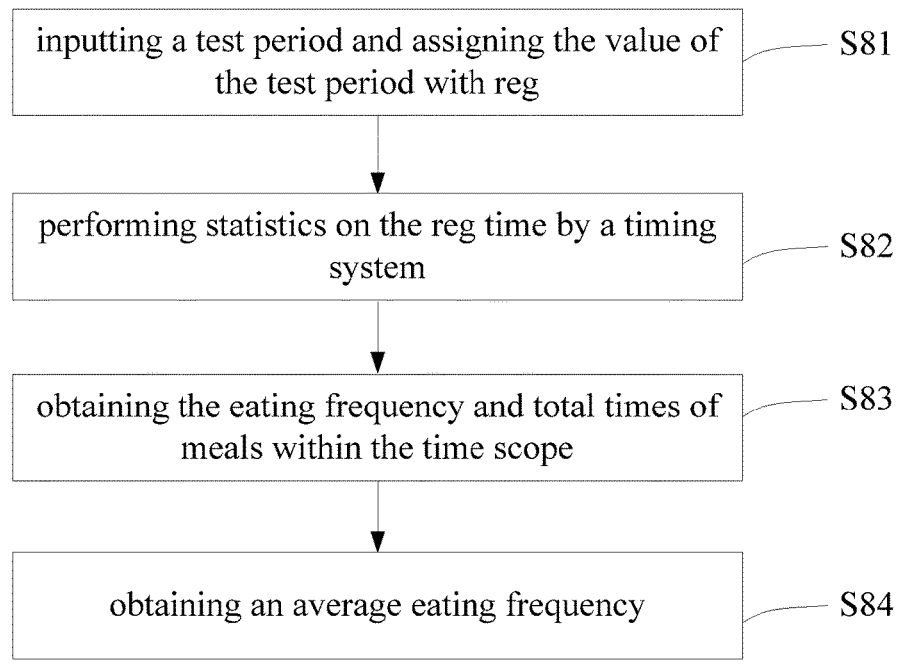
FIG. 8 is a schematic flow chart of an approach of calculating an reference frequency according to one embodiment of the present disclosure.

Reference is made to FIG. 8, which is schematic flow chart of an approach of calculating the reference frequency according to one embodiment of the present disclosure.

The approach includes: step S81, inputting a test period and assigning the value of the test period with reg; step S82, performing statistics on the reg time by a timing system; step S83, obtaining the eating frequency and total times of meals within the time scope of the test period; and step S84, obtaining an average eating frequency.

Preferred implementations of the present disclosure are described above. It should be noted that, the ordinary skilled in the art can make various improvements and polishes without departing from the principle of the present disclosure, and those improvements and polishes all fall within the scope of protection of the present disclosure.

What is claimed is:

1. A wearable device, wearable on an arm of a user, comprising an acceleration sensor, an amplifier-filter, an analog-to-digital converter, a microprogrammed control unit (MCU), a random access memory, a digital-to-analog converter, an alarm and a display unit;

wherein the acceleration sensor is configured to acquire acceleration information of the arm of the user and convert the acceleration information into an analog electric signal;

the amplifier-filter is connected to the acceleration sensor and configured to amplify and filter the analog electric signal;

the analog-to-digital converter is connected to the amplifier-filter and configured to convert the analog electric signal already amplified and filtered by the amplifier-filter into a digital signal;

the MCU is configured to calculate times of eating of the user within a predetermined duration based on the digital signal, compare an eating frequency with a reference frequency, and generate a first alarming signal if determining through comparison that the eating frequency is larger than or equal to the reference frequency;

the random access memory is connected to the MCU and configured to store the reference frequency;

the digital-to-analog converter is connected to the MCU and configured to convert the eating frequency of the user into an analog signal and send the analog signal to the display unit;

the display unit is connected to the digital-to-analog converter and configured to display the eating frequency; and the alarm is connected to the MCU and configured to alarm in response to the first alarming signal, wherein the MCU is further configured to calculate an average eating frequency of the user within a preset test period and set the average eating frequency as the reference frequency; and the wearable device further comprises a storage configured to store the reference frequency; and wherein the MCU is further configured to set a test mode or an eating monitoring mode, when the test mode is set, the MCU is configured to calculate the average eating frequency of the user within the preset test period and set the average eating frequency as the reference frequency, and when the eating monitoring mode is set, the MCU is configured to compare the eating frequency with the reference frequency and generate the first alarming signal if determining through comparison that the eating frequency is larger than or equal to the reference frequency.

2. The wearable device according to claim 1, wherein the wearable device is a bracelet.

3. The wearable device according to claim 1, wherein the alarm is a vibration alarm, an audio alarm, a caution light or the display unit.

4. A wearable device, wearable on an arm of a user, comprising:

an acceleration sensor, configured to acquire acceleration information of the arm of the user;

a processing unit connected to the acceleration sensor, configured to calculate times of eating performed by the user in a predetermined duration based on the acceleration information and obtain an eating frequency of the user;

a comparing unit connected to the processing unit, configured to compare the eating frequency with a reference frequency and generate a first alarming signal if determining through comparison that the eating frequency is equal to or larger than the reference frequency; and an alarm connected to the comparing unit, configured to alarm upon reception of the first alarming signal, wherein the wearable device further comprises:

a calculating unit connected to the processing unit, configured to calculate an average eating frequency of the user within a preset test period and set the average eating frequency as the reference frequency; and a storage connected to the calculating unit, configured to store the reference frequency, wherein the wearable device further comprises:

a mode setting unit, configured to set a test mode and an eating monitoring mode, and a controller connected to the mode setting unit, configured to control the calculating unit to operate and control the comparing unit not to operate when the test mode is set, and control the comparing unit to operate and control the calculating unit not to operate when the eating monitoring mode is set.

5. The wearable device according to claim 4, further comprising:

a display unit, connected to the comparing unit and configured to display the eating frequency of the user upon reception of the first alarming signal.

6. The wearable device according to claim 4, further comprising:

a frequency setting unit configured to provide a frequency setting interface for the user to set the reference frequency, wherein the storage connected to the frequency setting unit and configured to store the reference frequency.

7. The wearable device according to claim 4, further comprising:

a controlling switch, configured to generate an on signal under control of the user and generate an off signal under control of the user, and a battery unit connected to the controlling switch, the acceleration sensor, the processing unit and the alarm, configured to provide electricity to the acceleration sensor, the processing unit and the alarm upon reception of the on signal and stop providing electricity to the acceleration sensor, the processing unit and the alarm upon reception of the off signal.

8. The wearable device according to claim 7, further comprising a counter connected to the processing unit, configured to count total times of eating of the user after being provided with electricity and generate a second alarming signal if the total times of eating exceed a preset threshold;

wherein the alarm is further configured to alarm upon reception of the second alarming signal, and the alarm alarms, upon reception of the second alarming signal, in a different way from alarming upon reception of the first alarming signal.

9. The wearable device according to claim 4, wherein the alarm is a vibration alarm, an audio alarm, a caution light or a display unit.

10. The wearable device according to claim 4, wherein the wearable device is a bracelet.

* * * * *